US012233030B2

(12) United States Patent
Cho et al.

(10) Patent No.: US 12,233,030 B2
(45) Date of Patent: Feb. 25, 2025

(54) DIE ROLL FOR FORMING SOFT GEL CAPSULES

(71) Applicant: CAPTEK Softgel International, Inc., Cerritos, CA (US)

(72) Inventors: Jung Ku Cho, Cerritos, CA (US); Bibu Philip George, Norwalk, CA (US); Byeong Yeop Lee, Los Angeles, CA (US); Steven Eikichi Quan, San Marcos, CA (US)

(73) Assignee: CAPTEK Softgel International, Inc., Cerritos, CA (US)

( * ) Notice: Subject to any disclaimer, the term of this patent is extended or adjusted under 35 U.S.C. 154(b) by 158 days.

(21) Appl. No.: 18/063,927

(22) Filed: Dec. 9, 2022

(65) Prior Publication Data

US 2023/0106844 A1    Apr. 6, 2023

Related U.S. Application Data

(60) Provisional application No. 63/369,097, filed on Jul. 22, 2022, provisional application No. 63/265,660, filed on Dec. 17, 2021.

(51) Int. Cl.
*A61J 3/07* (2006.01)
*A61K 9/48* (2006.01)

(52) U.S. Cl.
CPC .............. *A61J 3/07* (2013.01); *A61K 9/4808* (2013.01)

(58) Field of Classification Search
CPC .................... A61J 3/07; A61K 9/4808
See application file for complete search history.

(56) References Cited

U.S. PATENT DOCUMENTS

| | | | | | |
|---|---|---|---|---|---|
| 2,513,852 | A | * | 7/1950 | Donofrio | B65B 9/042 |
| | | | | | 53/204 |
| 2,663,130 | A | * | 12/1953 | Donofrio | A61J 3/07 |
| | | | | | 264/DIG. 37 |
| 2,690,038 | A | * | 9/1954 | Stirn | A61J 3/07 |
| | | | | | 264/DIG. 37 |
| 2,697,315 | A | * | 12/1954 | Stirn | A61J 3/07 |
| | | | | | 53/546 |
| 2,697,317 | A | * | 12/1954 | Stirn | A61J 3/07 |
| | | | | | 15/345 |
| 2,775,080 | A | * | 12/1956 | Stirn | A61J 3/07 |
| | | | | | 264/DIG. 37 |
| 3,092,942 | A | * | 6/1963 | Chasman | A61J 3/07 |
| | | | | | 418/16 |
| 3,124,840 | A | * | 3/1964 | Taylor et al. | B29C 51/225 |
| | | | | | 425/134 |
| 10,195,115 | B2 | * | 2/2019 | Puckett | A61K 9/4808 |
| 2001/0022066 | A1 | * | 9/2001 | Stolz | B65B 9/023 |
| | | | | | 53/560 |

* cited by examiner

*Primary Examiner* — Lucas E. A. Palmer
(74) *Attorney, Agent, or Firm* — FisherBroyles, LLP

(57) ABSTRACT

A die roll may be used to form soft gel capsules via rotary encapsulation. The die roll may include a plurality of cavities. At least one cavity includes a cavity length, and the die roll includes a first die surface provided along a first portion of the cavity length and a second die surface provided along a second portion of the cavity length. The second die surface may be elevated relative to the first die surface.

17 Claims, 8 Drawing Sheets

DIE ROLL FOR FORMING SOFT GEL CAPSULES

REFERENCE TO RELATED APPLICATIONS

This application claims the benefit of U.S. Provisional Patent Application No. 63/265,660, filed on Dec. 17, 2021, and entitled DIE ROLL FOR FORMING SOFT GEL CAPSULES, and the benefit of U.S. Provisional Patent Application No. 63/369,097, filed on Jul. 22, 2022, and entitled DIE ROLL FOR FORMING SOFT GEL CAPSULES, both of which are hereby incorporated by reference in their entireties.

FIELD OF THE INVENTION

This application relates to soft gel capsules, and more particularly to rotary encapsulation die rolls and associated systems and methods for encapsulating fill material in soft gel capsules.

BACKGROUND

Rotary encapsulation die rolls can be used to encapsulate fill material in soft gel capsules. Two of the main quality issues that occur during encapsulation of soft gel capsules are poor sealing strength and crooked sealing (pinched sealing when at extreme). Both of those can result in leaking of the enclosed fill material.

SUMMARY

Embodiments covered by this patent are defined by the claims below, not this summary. This summary is a high-level overview of various embodiments and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

Described herein is a new die roll design for reducing and/or minimizing negative results that otherwise can be caused by inconsistent formulations, imprecise operating parameters, and/or human error. The inventive die roll design described herein lesses or prevents soft gel capsules leakage as compared to soft gel capsules made from conventional die roll designs. The die rolls described herein maximize the leading and trailing seam (relatively). The inventive die rolls reduce and/or prevent crooked corner sealing (pinched corner sealing when at extreme) and improve sealing strength. In certain embodiments, the inventive die roll designs described herein help prevent or reduce crooked sealing and pinched corner sealing (both crooked and pinched corner sealing occurs when there are insufficient room for gel ribbon during encapsulation; pinched corner sealing occurring at even thicker gel ribbon) and promote stronger sealing in comparison to the conventional design. The improved sealing may help prevent insufficient quality that may result from other quality issues.

Various implementations described in the present disclosure can include additional systems, methods, features, and advantages, which cannot necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The specification makes reference to the following appended figures, in which use of like reference numerals in different figures is intended to illustrate like or analogous components.

DETAILED DESCRIPTION

Described herein are improved die rolls for encapsulating a fill material in soft gel capsules. In certain embodiments, the die rolls provided herein may produce soft gel capsules with improved sealing and sealing strength compared to traditional die rolls. Various other benefits and advantages may be realized with the systems and methods provided herein, and the aforementioned advantages should not be considered limiting.

FIGS. 1-6 illustrate a die roll 100 according to various embodiments. The die roll 100 generally includes a first die surface 102, a second die surface 104, and one or more cavities 106. In various embodiments and as discussed in detail below, the second die surface 104 is elevated relative to the first die surface 102. For comparison, in a conventional die roll design, the distance from the land surface to the outer die surface is equal around the cavity.

Figure 3:
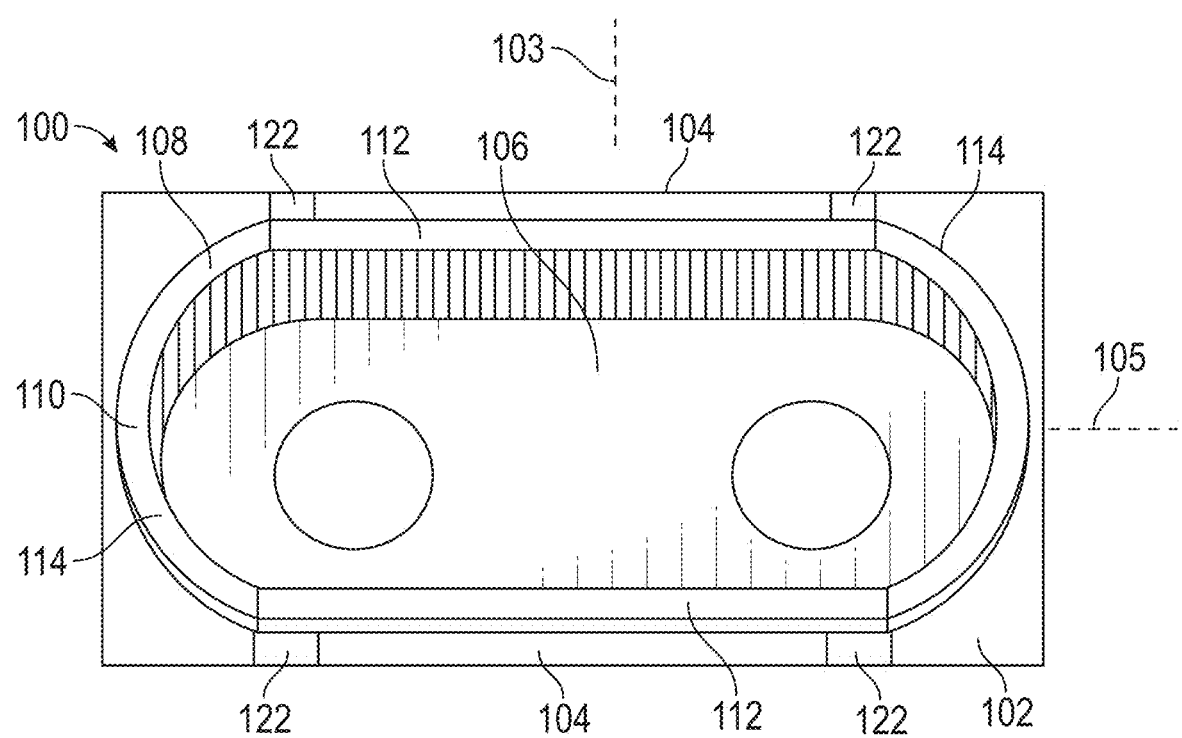
FIG. 3 is a schematic of a portion of a die roll according to embodiments.

Each cavity 106 has a cavity wall 108 with a surface or land 110 that is elevated relative to both the first die surface 102 and the second die surface 104. Referring to FIG. 3, the cavity 106 may have a shape that is symmetrical about both a lateral axis 103 and a longitudinal axis 105 of the cavity 106. Non-limiting examples of shapes of the cavity 106 may be oval, round, etc. In the embodiment illustrated, the cavity 106 is an elongated shape such that the cavity wall 108 includes side portions 112 and end portions 114. The side portions 112 may be the leading and trailing portions of the cavity 106 as the die roll 100 is rotated (see, e.g., FIG. 7), and the end portions 114 may be corners, sides, or other transition portions between the leading and trailing side portions 112 of the cavity 106. Reference to the portions 112 as "side" portions and similarly reference to the portions 114 as "end" portions should not be considered limiting or intending to require any particular shape of the cavities 106; rather, such terms are used to merely distinguish different regions or portions of the cavity wall 108.

Figure 7:
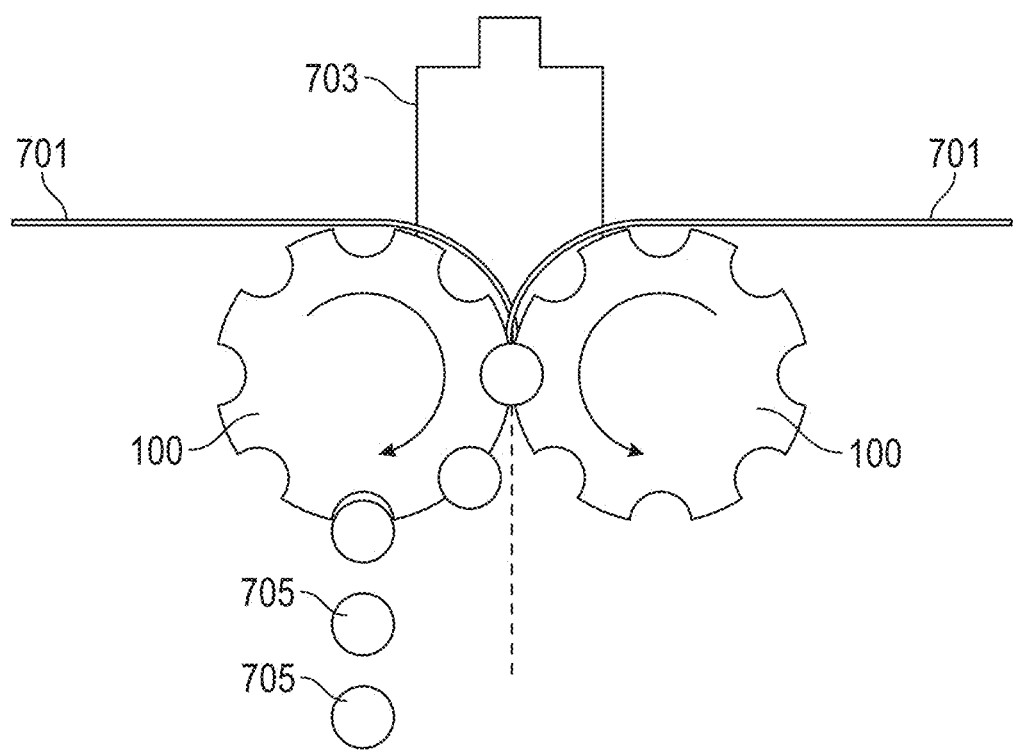
FIG. 7 is a schematic of a die roll in use according to embodiments.

Referring briefly to FIG. 7, during an encapsulation process of with a cavity and sealing of a softgel capsule 705, as gelatin ribbons 701 are cast and eventually pass in between the die rolls 100, the balance of the injection wedge assembly 703, the die rolls 100, and coated gelatin ribbons 701 may prevent or minimize external sources (such as but not limited to air) from entering. The gel ribbons 701 continue to move as the drum, rollers and die rolls 100 rotate, and the balance between the components allows space in between the ribbons 701 and the wedges 703 at the injection point to be enclosed tightly. Filling of a capsule may start before a leading seam starts sealing. The leading seam forms as the gel is extruded towards inside the cavity as the die rotates (e.g., the leading seam is formed between side portions 112 on the die rolls 100). The trailing seam of a capsule (e.g., formed between the next set of side portions 112) may seal after the fill is injected into the cavity, but the gel does not seal inward the cavity in degree as done for the leading seam.

The pinched sealing traditionally occurs usually on the edge/corner of the seam right before the transition of the leading seam to trailing seam. Such pinched sealing may be because at high gel ribbon thickness, the amount of gel may highly exceed the amount needed for sealing; therefore, even after the leading seam seals there may be excess gel which inhibits proper sealing. According to embodiments of the invention, the end portions 114 provide additional room for excess gel at the corners, sides, or transitions of the capsules 705. In other words, the first die surface 102 on the corner will be lower than the second die surface 104 of the side that leads and trails the capsule sealing. Such features may be used with any cavity shape as desired and is not limited to cavities with narrower sides of the cavity not being the corner side nor to dies with special cavity shapes.

In the embodiment illustrated in FIG. 3, the end portions 114 may have a curvature as illustrated in FIG. 3, for example, and the side portions 112 may be generally planar or linear. In such embodiments, the side portions 112 may be substantially parallel to each other (i.e., the side portions 112 may be long parallel sections of the walls 108). However, as mentioned, in other embodiments, the cavity 106 may be other shapes as desired that are symmetrical about the lateral axis 103 and the longitudinal axis 105.

Figure 5:
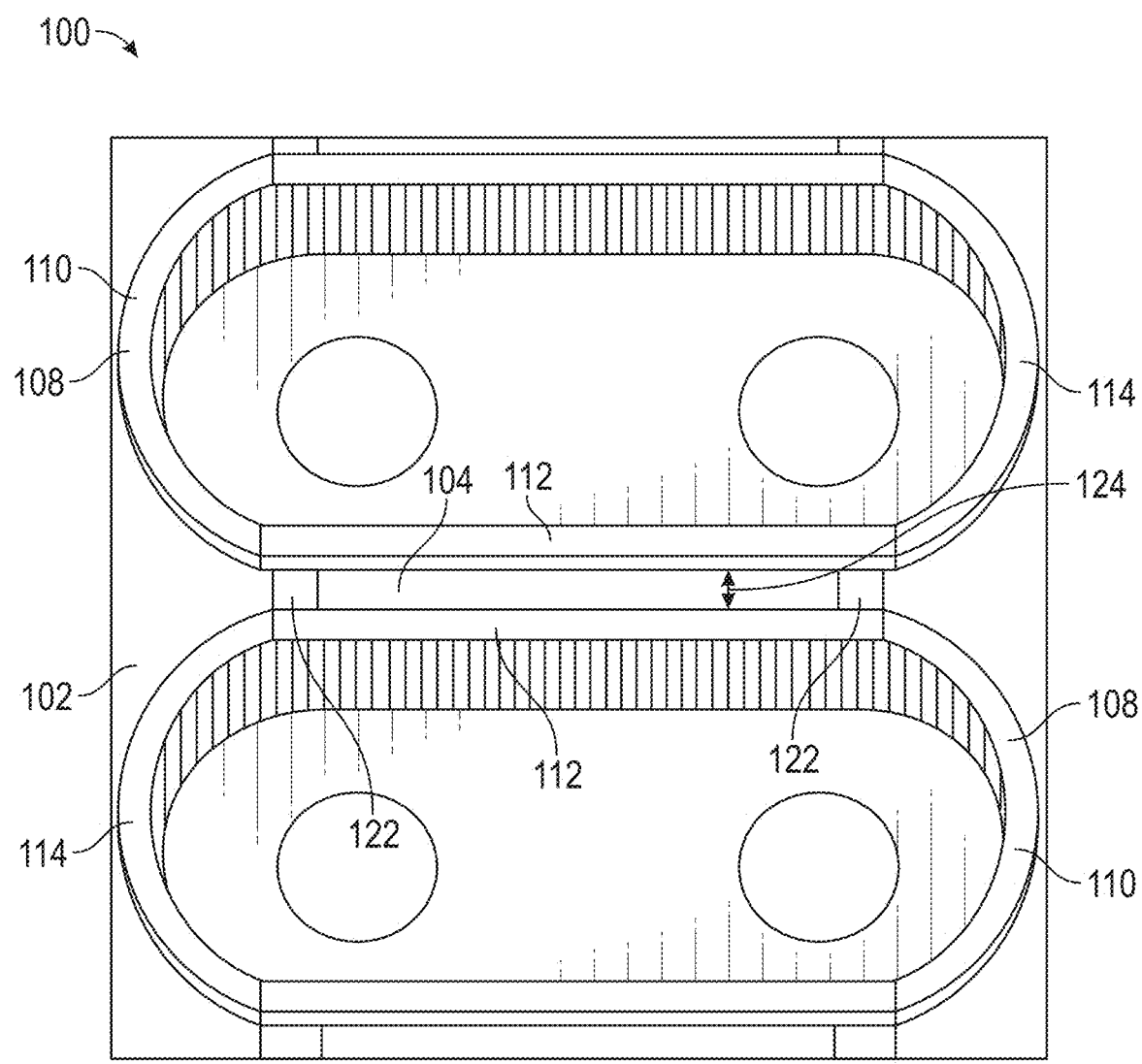
FIG. 5 is a schematic of a portion of a die roll according to embodiments showing two adjacent cavities.
Figure 6:
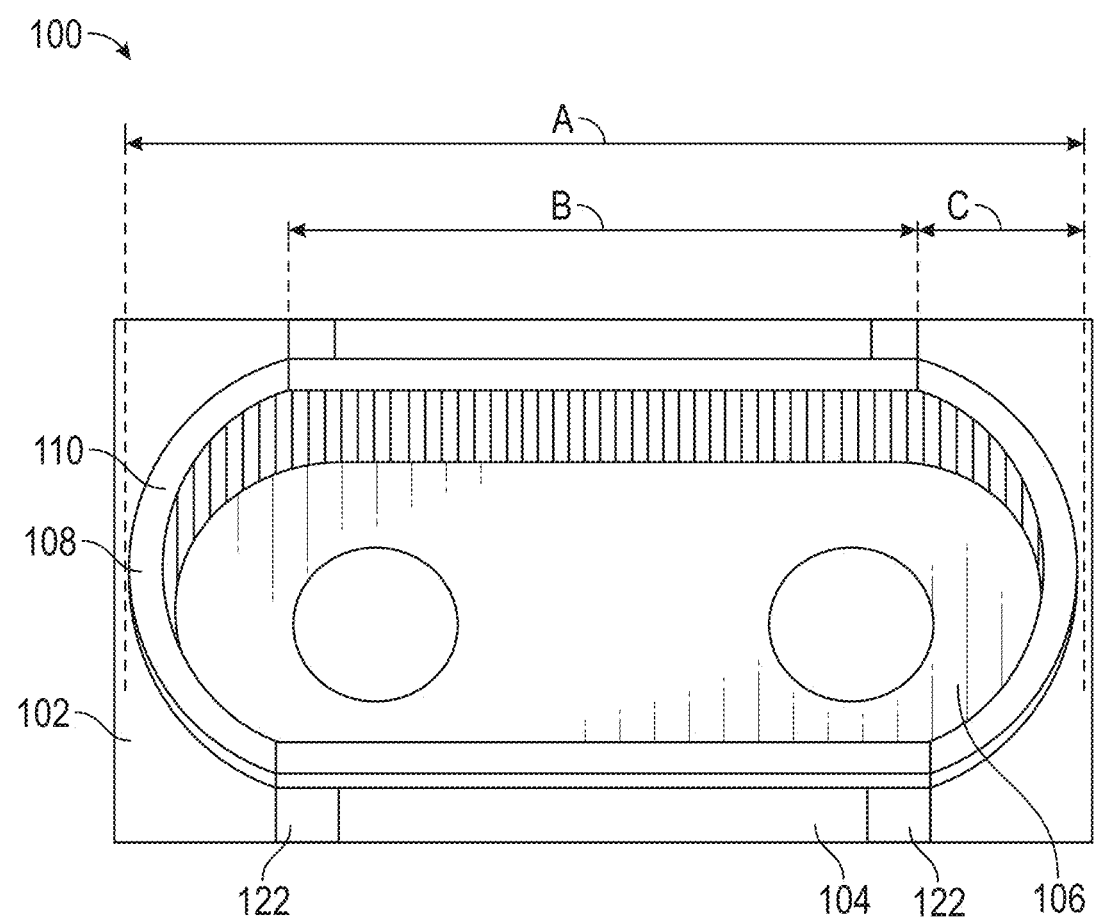
FIG. 6 is a schematic of a portion of a die roll according to embodiments.

In various embodiments and as illustrated in FIG. 6, each cavity has an overall length A, which is a distance between the outer edges of the end portions 114. The overall length A illustrated should not be considered limiting, an in various embodiments the overall length A may be lengths greater than or less than what is illustrated in FIG. 6. The cavities 106 may have various depths as desired, and the depths illustrated in FIGS. 1-6 should not be considered limiting.

As best illustrated in FIGS. 3-6, the second (elevated) die surface 104 may be provided adjacent to the side portions 112 of the cavities 106, and the first die surface 102 may be provided adjacent to the end portions 114 of the cavities 106. As mentioned, the cavities 106 may be other shapes as desired and is not limited to the cavities illustrated in FIGS. 3-6.

Figure 4A:
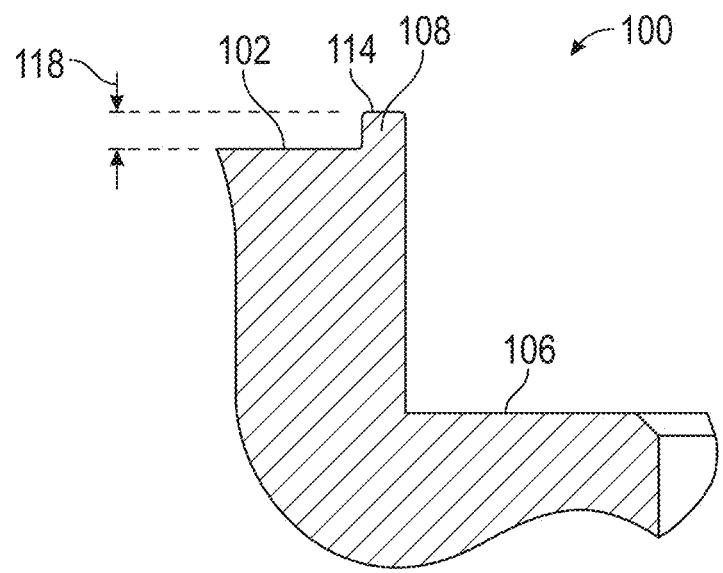
FIGS. 4A-B are sectional views of a cavity of a die roll according to embodiments.
Figure 4B:
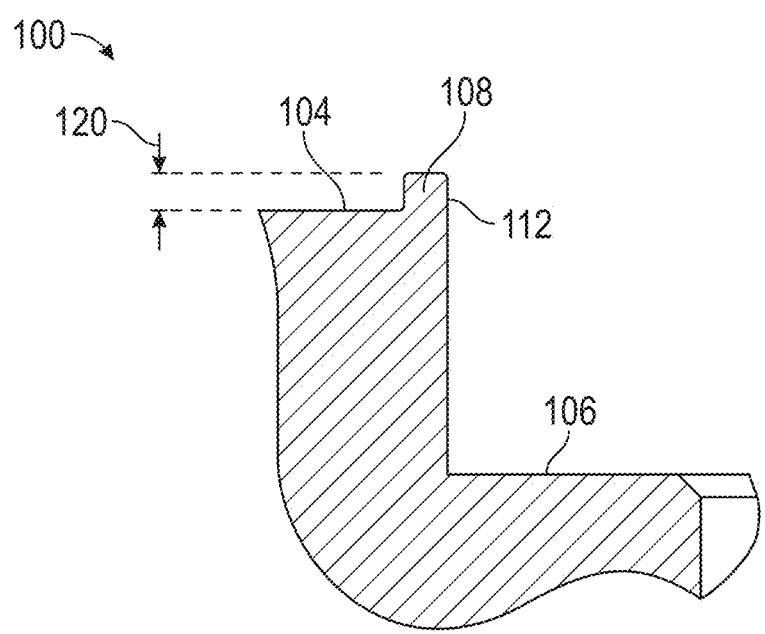

In certain embodiments, and as illustrated in FIGS. 4A-B, a first height 118 may be measured from the first die surface 102 to the land 110, and a second height 120 may be measured from the second die surface 104 to the land 110.

The second height 120 is less than the first height 118 according to embodiments of the disclosure. In certain embodiments, the relative difference in depth and actual depth of the first height 118 and second height 120 may be adjusted or otherwise controlled based on a standard gelatin ribbon thickness that the die roll 100 has been designed to utilize when the die is used as a tooling for encapsulation. In one non-limiting embodiment, the second height 120 may be about 0.15 mm less than the first height 118, although in other embodiments the difference between the heights 118, 120 may be as otherwise desired. In fact, the relation is dependent on the standard target gel ribbon thickness that the die roll is designed for when utilized as a tooling for encapsulation. It thus should be understood that the specific dimensions shown are for one specific non-limiting embodiment and are not intended to limit the invention. For example, in some embodiments, the second height 120 is at a normal land to outer die roll surface height and the first height 118 is slightly deeper than the second height 120. In other embodiments, the first height 118 is at a normal land to outer die roll surface height and the second height 120 is slightly shallower than the first height 118. This difference between heights 118, 120 gives sufficient room for thick gelatin ribbon to seal without forming crooked seam sealing. This is true, even when the gelatin ribbon is much thicker than the target thickness that the die roll is designed to utilize if the second height 120 is uniform around the cavity 106. The die roll 100 design makes the relevant point at which the occupied amount of gel affects the corner sealing at a much greater gelatin ribbon thickness. As mentioned, the relative heights 118, 120 may be different and/or otherwise controlled to utilize various sized ribbons as desired.

In certain embodiments, and as best illustrated in FIGS. 3, 5, and 6, transition surfaces 122 may be provided between the first die surface 102 and the second die surface 104. The transition surfaces may be provided at various slopes or angles relative to the first die surface 102 and/or the second die surface 104 as desired. The transition surfaces 122 as such may have various lengths as desired. In one non-limiting embodiment, a length of each transition surface 122 along a particular cavity 106 may be from about 0.1 mm to about 2 mm; however, in other embodiments, the transition surfaces 122 may have other lengths as desired.

In various embodiments, and as illustrated in FIG. 6, a length B may be a length of the elevated surfaces (e.g., the second die surface 104 and/or the transition surfaces 122) along the cavities 106. A length C may be a length of the first (non-elevated) die surface 102 along the cavities 106. The length B and the length C together are equal to the overall length A of the cavity 106. In some embodiments, the length B may be about 60% to about 80% the overall length A, and the length C may be about 10% to about 20% the overall length A. In various embodiments, the length B may allow for additional gelatin at the elevated surfaces to be extruded inward during encapsulation, resulting in smoother and stronger sealing.

Referring to FIG. 5, a distance 124 between the end portions 114 of adjacent cavities 106 is narrower than conventional die roll designs. Resultantly, the volume and cross-sectional area of the second die surface 104 in between different cavities 106 are narrower/smaller for the inventive die roll than for a conventional die roll design. The narrower space between adjacent cavities 106 provides less room at the sealing point for gel to push out and collect. The narrower space between adjacent cavities 106 also provides stronger sealing than conventional die rolls by promoting extrusion of gel when sealing.

Referring to FIG. 7, during an encapsulation process, gel ribbons 701 and a fill material 703 are fed between adjacent die rolls 100 to form the soft gel capsule 705. As the gel ribbons 701 approaches the center point, fill injection occurs. During this process, the beginning sealing which seals (usually) after the fill starts to inject is the leading seam, and the trail end sealing after all fill is injected and thus completing the fill encapsulation is the trailing seam.

The inventive die roll 100 design reduces or eliminates crooked or pinched corner seams that result due to the excess of gel between the corners of the die roll cavities 106 in relation to the respective sealing parameter of the cavities 106 resulting in a smooth sealing. Conventional die roll designs include a single outer die surface around the cavity and thus the distance from the land 110 to the outer die surface is equal around the cavity. In such conventional die roll designs, crooked or pinched seam sealing can result from using thicker ribbon than intended for the die roll 100 design. When the ribbon thickness is much thicker than that intended for the die roll design, there will be insufficient room at the corners for the gelatin to seal properly. The excess amount of gel present at the corners interferes with the sealing in that area, resulting in unsmooth sealing which results in crooked seam and eventually pinched seam sealing as the excess gel amount increases. The ratio between the respective sealing area in relation to the amount of gel occupying the area between the cavities decreases as gelatin ribbon thickness decreases; therefore, the aforementioned issue does not occur when the utilized gelatin ribbon is thinner or at a die roll design's recommended maximum gelatin ribbon thickness. Although same applies for the inventive die, its design allows higher tolerance of ribbon thickness above the design's recommended maximum gel ribbon thickness.

In the case of the long second die surface 104 between adjacent cavities 106 and having the reduced distance 124, the area between the side portions 112 of adjacent cavities 106 is much smaller in volume as in relation to the corner and in relation to the relative parameter of the capsule sealing that they occupy, and the aforementioned problem for the corner sealing does not apply. At a range of the usual gelatin ribbon thickness utilized during encapsulation, the gelatin ribbons are able to be push inward and seal during the encapsulation process on the long side portions 112 without trouble.

Figure 10:
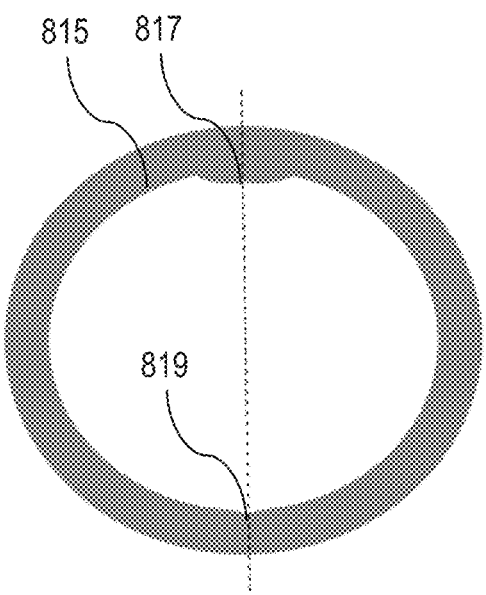

The basic concept of the design for improving sealing strength is shown in FIG. 5. As explained earlier, unlike the corner, which needs additional volume to prevent pinched seam sealing when there is a high ratio of gelatin ribbon around the die roll in relation to the respective sealing area, the same is not applicable for the adjacent (usually symmetrical, sometimes parallel) base. Thus, for conventional die rolls and as illustrated in FIG. 10, when the utilized ribbon thickness is reasonably thick, it creates a thick leading seam and likely an acceptable trailing seam, but due to insufficient room on the corner results in crooked or even pinched sealing. When the utilized ribbon thickness is the standard that the die is designed for, although not noticeably thick, it creates reasonable seam without crooked or pinched sealing on the corner. When the utilized ribbon thickness is reasonably thin, both the leading and trailing seam may become noticeably weak (see, e.g., FIG. 12), as there is not enough gelatin to push inward to form the seam. Unlike the leading sealing, where gel is extruded towards inside the cavity when sealing, gel is not pushed toward the cavity when the trailing sealing occurs, resulting in a weaker seam as compared to the leading seam.

Figure 9:
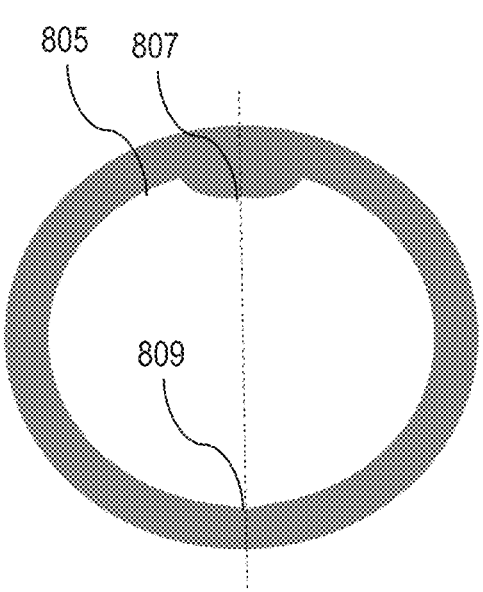
FIGS. 9, 10, 11 and 12 illustrates leading and trailing seam of a capsules formed using die roll of FIG. 1 or a conventional die, but at different relative gel ribbon thickness in relation to the standard gel ribbon thickness the dies have been designed to encapsulate.

The distance 124 between the symmetrical and/or parallel portions of cavity lands 110 of adjacent cavities 106, and resultantly the volume and cross-sectional area of the long second (elevated) die surface 104 between adjacent cavities 106 are narrower/smaller for the inventive die roll 100 described herein as compared to a conventional die roll design. This allows formation of a sufficiently thick leading seam at lower ribbon thickness (see, e.g., FIG. 11) than a conventional die roll and comparably even a thicker trailing seam (see, e.g., FIG. 11). The design also allows for a thicker leading and trailing seam if the utilized ribbon thickness is the standard that the die is designed for (see, e.g., FIG. 10) as if utilizing a ribbon reasonably thicker than the standard thickness designed for a conventional die utilized for encapsulation without resulting in crooked seam or pinched seam on the corners. In fact, the design expands the limit of thickness over the designed thickness standard at which crooked or pinched sealing begins to appear, allowing even stronger leading sealing before crooked or pinched sealing begins appearing on the corner (see, e.g., FIG. 9) The example figures discussed below show the expected results of the ring sample of a product seam when conventional or the proposed design is utilized at different gelatin ribbon thickness. Based on the concepts of the design, the proposed design allows for a higher and lower limit of gelatin ribbon above and below the standard ribbon thickness at which the utilized die is designed where a product can seal robustly or reasonably robustly without outlining cosmetic or quality defects on the encapsulated product.

Examples

The following procedure was followed:
1. Select a product fit for the comparison analysis:
2. Encapsulate about half of tray of products using each die roll design at gelatin ribbon thickness reasonable thicker than the standard gelatin ribbon thickness that the utilized die is designed for.
3. Directly receive and spread capsules on tray without tumble drying and air dry in drying room until fully dried.
4. Visually analyze the appearance of the capsules and verify if a pinched seam sealing has formed on the capsule corner.
5. Summarize and conclude results.

Figure 8B:
FIG. 8B illustrates a sample of capsules formed using a conventional die roll.
Figure 8A:
FIG. 8A illustrates a sample of capsules formed using a die roll according to embodiments.

Referring to FIGS. 8A-B, ribbon thickness was set reasonably above the standard the utilized dies are designed to utilize to verify both the sealing performance of the two die roll designs and if either sample group encapsulated using each of the two die rolls have presence of crooked or pinched seam sealing at their corner.

FIG. 8A illustrates capsules 805 formed using the die roll 100 and FIG. 8B illustrates capsules 815 formed using a conventional die roll and using gel ribbons at identical gel ribbon thickness reasonable thicker than the standard that the two dies are designed to utilize. Both the conventional and die roll 100 utilized for the comparison analysis are designed to utilized identical standard gelatin ribbon thickness.

Figure 1:
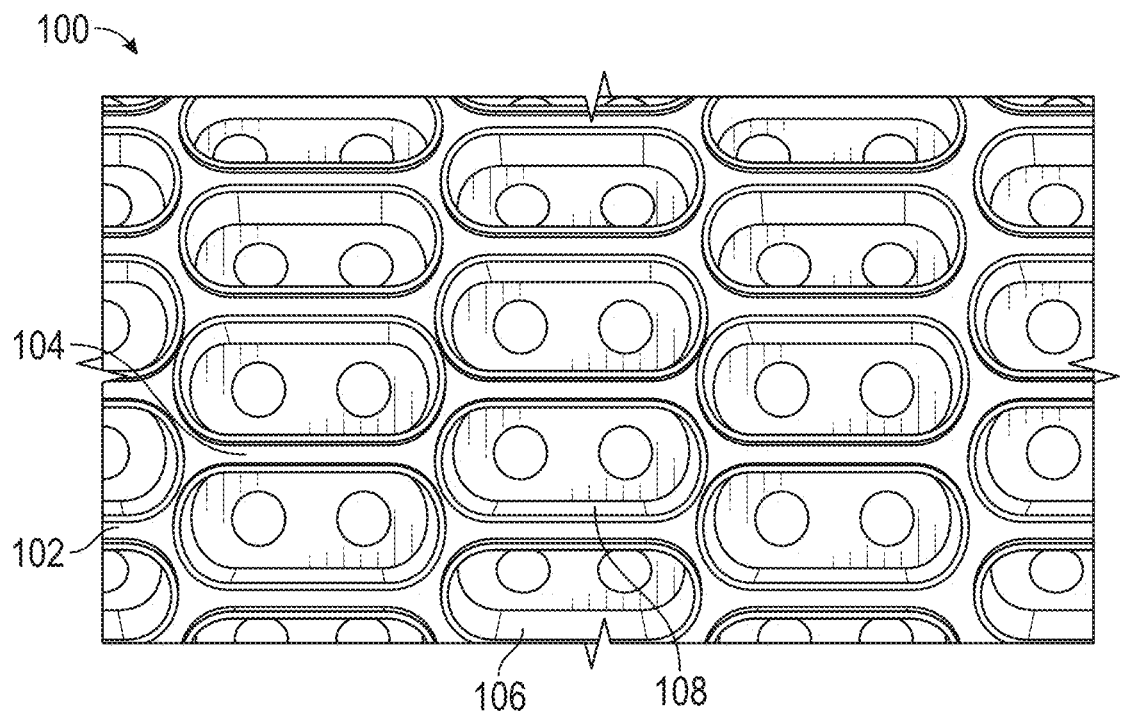
FIG. 1 is a photograph of a portion of a die roll according to embodiments.
Figure 2:
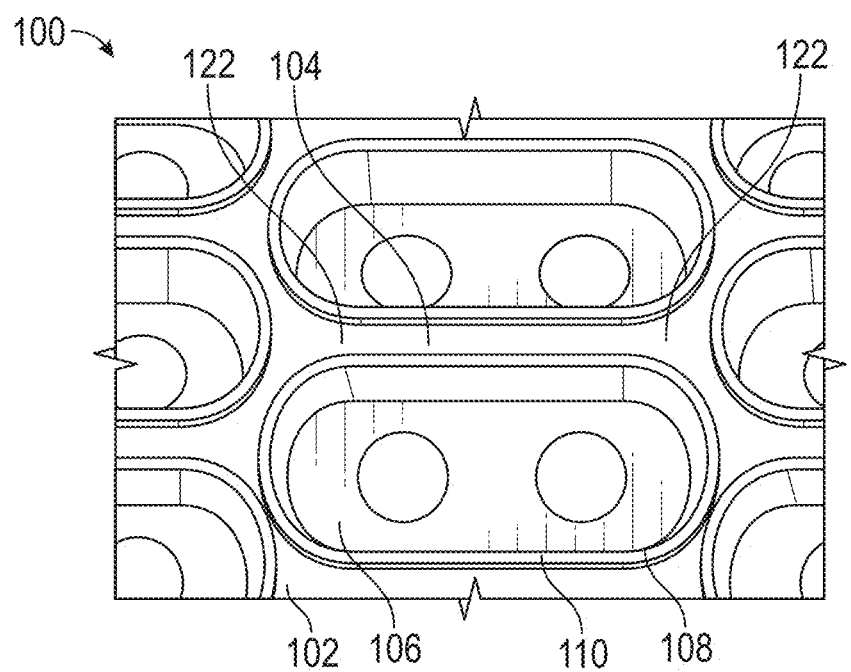
FIG. 2 is another photograph of the die roll of FIG. 1.

As mentioned earlier, FIGS. 9, 10, 11 and 12 illustrates leading and trailing seam of capsules formed using die roll of FIG. 1 (die roll 100) or a conventional die, but at a different relative gel ribbon thickness in relation to standard gel ribbon thickness the dies have been designed to encapsulate. Amongst the figures, FIG. 9 corresponds to the representative sample of a ring sample of capsules 805 with leading seam 807 and trailing seam 809, and FIG. 10 corresponds to the representative sample of a ring sample of capsules 815 with leading seam 817 and trailing seam 819.

As illustrated by these examples prepared with a thick gelatin ribbon, it can be seen that the trailing seams 809, 819 sealing of both the inventive die roll and the conventional die roll are robust and both die rolls formed a seam that folded toward the inside of the softgel. Also, the trailing seams provided by both designs are acceptable. From the evaluation of the ring sample, it can be seen that the inventive die roll design at least is equivalent to the conventional die roll with regard to seam thickness when encapsulating product at the tested gelatin ribbon thickness. However, referring to FIGS. 8A and 8B, although crooked or pinched sealing is not present on capsules encapsulated utilizing the inventive die (see, e.g. FIG. 8A), both crooked and pinched sealing are present on capsules encapsulated using the conventional die (see, e.g. FIG. 8B). From the evaluation of the capsule sample, it can be seen that the inventive die roll design has proven that it has higher limits in utilizing gelatin ribbon above the standard gelatin ribbon thickness that it has been designed to utilize before forming crooked or pinched sealing on the encapsulated capsule's corners.

Similarly, FIGS. 11 and 12 corresponds to the conceptual sealing performance of the two die roll designs (die roll 100 and conventional die roll), if a product was selected and ribbon thickness was set reasonably below the standard gelatin ribbon thickness the two die rolls are designed to utilize.

Figure 11:
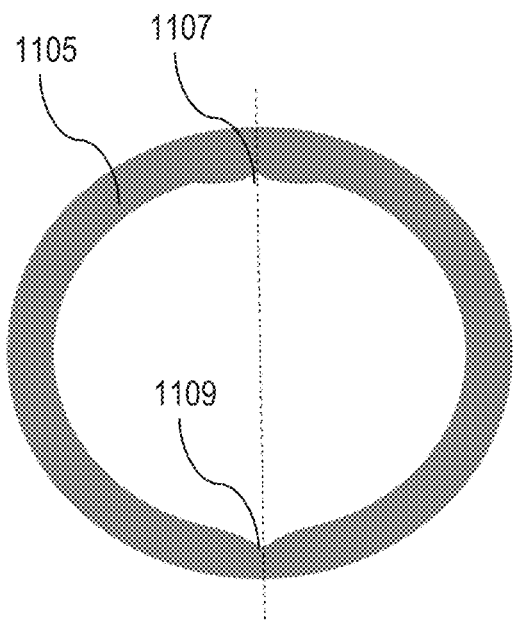
Figure 12:
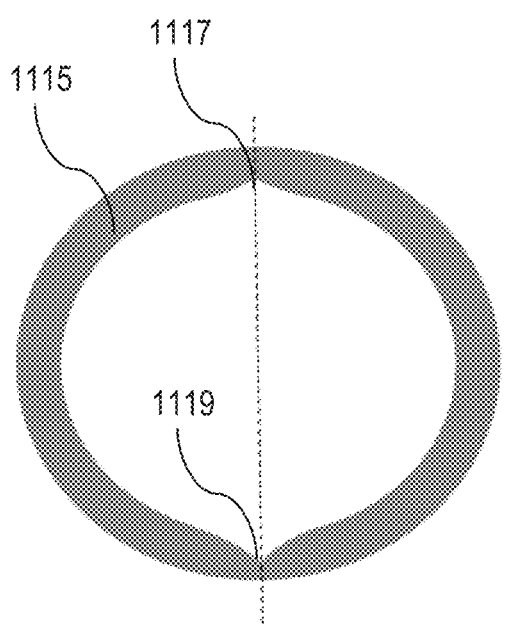

FIG. 11 corresponds to a representative sample of ring sample with leading seam 1107 and trailing seam 1109 of a capsule 1105 formed using the die roll 100, and FIG. 12 corresponds to a representative sample of ring sample with leading seam 1117 and trailing seam 1119 of a capsule 1115 formed using a conventional die roll and using gel ribbons having a ribbon thickness reasonable below the standard that the two dies are designed to utilize. As illustrated by these examples corresponding to when the two dies are prepared with lower ribbon thickness, the inventive die roll will provide both leading and trailing seam equivalent to 1107 and 1109 much stronger that the seams 1117 and 1119 expected for the conventional die roll. Considering all of the results and concept, the inventive die roll provides results equivalent to or better than the conventional die roll, and the inventive die roll provides better sealing at the lower gelatin ribbon thickness.

A collection of exemplary embodiments is provided below, including at least some explicitly enumerated as "Embodiments" providing additional description of a variety of example embodiments in accordance with the concepts described herein. These embodiments are not meant to be mutually exclusive, exhaustive, or restrictive; and the disclosure not limited to these example embodiments but rather encompasses all possible modifications and variations within the scope of the issued claims and their equivalents.

Embodiment 1. A die roll for rotary encapsulation, the die roll comprising: a cavity comprising a land; a first die surface adjacent to a first portion of the cavity; and a second die surface adjacent to a second portion of the cavity, wherein the land is elevated above the first die surface and the second die surface, and wherein a distance between the land to the first die surface is different from a distance between the land and the second die surface.

Embodiment 2. The die roll of any of the preceding or subsequent embodiments or combination of embodiments, wherein the cavity is a first cavity, and wherein the die roll comprises a second cavity adjacent to the first cavity, and wherein at least the second die surface is between the first cavity and the second cavity.

Embodiment 3. The die roll of any of the preceding or subsequent embodiments or combination of embodiments, wherein the second cavity comprises a land, and wherein the second die surface is between adjacent parallel portions of the land of the first cavity and the land of the second cavity.

Embodiment 4. The die roll of any of the preceding or subsequent embodiments or combination of embodiments, wherein the distance between the land to the first die surface is greater than the distance between the land and the second die surface.

Embodiment 5. The die roll of any of the preceding or subsequent embodiments or combination of embodiments, wherein the land comprises end portions and side portions, wherein the side portions extend parallel to each other.

Embodiment 6. The die roll of any of the preceding or subsequent embodiments or combination of embodiments, wherein the second die surface is adjacent to the side portions and the first die surface is adjacent to the end portions.

Embodiment 7. The die roll of any of the preceding or subsequent embodiments or combination of embodiments, wherein the cavity comprises a cavity length, wherein the first die surface is provided along a first portion of the cavity length, wherein the second portion is provided along a second portion of the cavity length, and wherein a length of the second portion is greater than a length of the first portion.

Embodiment 8. The die roll of any of the preceding or subsequent embodiments or combination of embodiments, further comprising a transition surface between the first die surface and the second die surface, wherein the transition surface extends at an oblique angle relative to the first die surface and the second die surface.

Embodiment 9. The die roll of any of the preceding or subsequent embodiments or combination of embodiments, wherein the transition surface is planar.

Embodiment 10. A method of forming a soft gel capsule, the method comprising feeding gel ribbons and a fill material between adjacent die rolls, wherein each die roll is a die roll of any of the preceding or subsequent embodiments or combination of embodiments.

Embodiment 11. A soft gel capsule formed by the method of any of the preceding or subsequent embodiments or combination of embodiments.

Embodiment 12. A die roll for rotary encapsulation, the die roll comprising: a cavity comprising a cavity length; a first die surface provided along a first portion of the cavity length; and a second die surface provided along a second portion of the cavity length, wherein the second die surface is elevated relative to the first die surface, and wherein a length of the second portion is greater than a length of the first portion.

Embodiment 13. The die roll of any of the preceding or subsequent embodiments or combination of embodiments, wherein the cavity comprises a cavity wall comprising side portions and end portions, wherein the second die surface is provided adjacent to the side portions of the cavity wall and the first die surface is provided adjacent to the end portions of the cavity wall.

Embodiment 14. The die roll of any of the preceding or subsequent embodiments or combination of embodiments, further comprising a transition surface extending between the first die surface and the second die surface, wherein the transition surface is sloped from the first die surface to the second die surface.

Embodiment 15. The die roll of any of the preceding or subsequent embodiments or combination of embodiments, wherein the cavity is a first cavity of a plurality of cavities, and wherein each cavity of the plurality of cavities comprises the cavity length, the first die surface provided along the first portion of the cavity length, and the second die surface provided along the second portion of the cavity length.

Embodiment 16. The die roll of any of the preceding or subsequent embodiments or combination of embodiments, wherein the cavity is a first cavity, wherein the die roll further comprises a second cavity adjacent to the first cavity, wherein each of the first cavity and the second cavity comprise a cavity wall, and wherein a portion of the cavity wall of the first cavity is parallel to a portion of the cavity wall of the second cavity along identical axis, and wherein the parallel portions of the cavity walls are adjacent to each other.

Embodiment 17. The die roll of any of the preceding or subsequent embodiments or combination of embodiments, wherein the second die surface is between the adjacent parallel portions of the cavity walls.

Embodiment 18. The die roll of any of the preceding or subsequent embodiments or combination of embodiments, wherein a difference in height between the first die surface and the second die surface is about 0.15 mm.

Embodiment 19. A method of forming a soft gel capsule, the method comprising feeding gel ribbons and a fill material between adjacent die rolls, wherein each die roll is a die roll of any of the preceding or subsequent embodiments or combination of embodiments.

Embodiment 20. A soft gel capsule formed by the method of any of the preceding or subsequent embodiments or combination of embodiments.

Embodiment 21. A die roll for rotary encapsulation, the die roll comprising: a first cavity and a second cavity adjacent to the first cavity, wherein each of the first cavity and the second cavity comprise a cavity wall, and wherein a portion of the cavity wall of the first cavity is parallel to a portion of the cavity wall of the second cavity along identical axis, and wherein the parallel portions of the cavity walls are adjacent to each other; a first die surface; and a second die surface, wherein the second die surface is between the adjacent parallel portions of the cavity walls, and wherein the second die surface is elevated relative to the first die surface.

Embodiment 22. A soft gel capsule formed using the die roll of any of any of the preceding or subsequent embodiments or combination of embodiments.

Embodiment 23. A method of forming soft gel capsules, the method comprising: feeding gel ribbons and a fill material between adjacent die rolls, wherein each die roll comprises a plurality of cavities, a first die surface, and a second die surface that is elevated relative to the first die surface.

The various aspects, embodiments, implementations or features of the described embodiments can be used separately or in any combination. In particular, it should be appreciated that the various elements of concepts from the figures may be combined without departing from the spirit or scope of the invention.

The use of the terms "a" and "an" and "the" and similar referents in the context of describing the invention (especially in the context of the following claims) are to be construed to cover both the singular and the plural, unless otherwise indicated herein or clearly contradicted by context. Directional references such as "up," "down," "top," "bottom," "left," "right," "front," and "back," among others, are intended to refer to the orientation as illustrated and described in the figure (or figures) to which the components and directions are referencing. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, or gradients thereof, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, the nearness of completion will be so as to have the same overall result as if absolute and total completion were obtained. As used herein, the term "about" refers to +/−5% of an indicated value or endpoints of an indicated range.

Preferred embodiments of this invention are described herein, including the best mode known to the inventors for carrying out the invention. The invention is susceptible to various modifications and alternative constructions, and certain shown exemplary embodiments thereof are shown in the drawings and have been described above in detail. Variations of those preferred embodiments, within the spirit of the present invention, may become apparent to those of ordinary skill in the art upon reading the foregoing description. The inventors expect skilled artisans to employ such variations as appropriate, and the inventors intend for the invention to be practiced otherwise than as specifically described herein. Accordingly, it should be understood that there is no intention to limit the invention to the specific form or forms disclosed, but on the contrary, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

That which is claimed:

1. A die roll for rotary encapsulation, the die roll comprising:
    a cavity comprising a land;
    a first die surface adjacent to a first portion of the cavity;
    a second die surface adjacent to a second portion of the cavity, and
    a transition surface between the first die surface and the second die surface that extends at an oblique angle relative to the first die surface and the second die surface;
    wherein the land is elevated above the first die surface and the second die surface, and
    wherein a distance between the land to the first die surface is different from a distance between the land and the second die surface.

2. The die roll of claim 1, wherein the cavity is a first cavity, and wherein the die roll comprises a second cavity adjacent to the first cavity, and wherein at least the second die surface is between the first cavity and the second cavity.

3. The die roll of claim 2, wherein the second cavity comprises a land, and wherein the second die surface is between adjacent parallel portions of the land of the first cavity and the land of the second cavity.

4. The die roll of claim 1, wherein the distance between the land to the first die surface is greater than the distance between the land and the second die surface.

5. The die roll of claim 1, wherein the land comprises end portions and side portions, wherein the side portions extend parallel to each other.

6. The die roll of claim 5, wherein the second die surface is adjacent to the side portions and the first die surface is adjacent to the end portions.

7. The die roll of claim 1, wherein the cavity comprises a cavity length, wherein the first die surface is provided along a first portion of the cavity length, wherein the second portion is provided along a second portion of the cavity length, and wherein a length of the second portion is greater than a length of the first portion.

8. The die roll of claim 1, wherein the transition surface is planar.

9. A method of forming a soft gel capsule, the method comprising feeding gel ribbons and a fill material between adjacent die rolls, wherein each die roll is a die roll according to claim 1.

10. A soft gel capsule formed by the method of claim 9.

11. A die roll for rotary encapsulation, the die roll comprising:
    a cavity comprising a cavity length;
    a first die surface provided along a first portion of the cavity length;
    a second die surface provided along a second portion of the cavity length, and
    a transition surface extending between the first die surface and the second die surface that is sloped from the first die surface to the second die surface;
    wherein the second die surface is elevated relative to the first die surface, and
    wherein a length of the second portion is greater than a length of the first portion.

12. The die roll of claim 11, wherein the cavity comprises a cavity wall comprising side portions and end portions, wherein the second die surface is provided adjacent to the side portions of the cavity wall and the first die surface is provided adjacent to the end portions of the cavity wall.

13. The die roll of claim 11, wherein the cavity is a first cavity of a plurality of cavities, and wherein each cavity of the plurality of cavities comprises the cavity length, the first die surface provided along the first portion of the cavity length, and the second die surface provided along the second portion of the cavity length.

14. The die roll of claim 11, wherein a difference in height between the first die surface and the second die surface is about 0.15 mm.

15. A method of forming a soft gel capsule, the method comprising feeding gel ribbons and a fill material between adjacent die rolls, wherein each die roll is a die roll according to claim 11.

16. A soft gel capsule formed by the method of claim 15.

17. A die roll for rotary encapsulation, the die roll comprising:
    a first cavity comprising a cavity length and having a first cavity wall;
    a second cavity adjacent to the first cavity and having a second cavity wall;
    a first die surface provided along a first portion of the cavity length; and
    a second die surface provided along a second portion of the cavity length, the second die surface being elevated relative to the first die surface, and a length of the second portion is greater than a length of the first portion
    wherein a portion of the first cavity wall of the first cavity is parallel to a portion of the second cavity wall of the second cavity along identical axis, and wherein the parallel portions of the cavity walls are adjacent to each other, and the second die surface is between the adjacent parallel portions of the cavity walls.

* * * * *